(12) United States Patent  
Riveline et al.

(10) Patent No.: US 9,304,125 B2
(45) Date of Patent: Apr. 5, 2016

(54) DEVICES AND METHODS FOR OBSERVING THE CELL DIVISION

(75) Inventors: Daniel Riveline, Strasbourg (FR); Axel Buguin, Paris (FR)

(73) Assignees: CENTRE NATIONAL DE LA RECHERCHE SCIENTIFIQUE, Paris (FR); ROCKEFELLER UNIVERSITY, New York, NY (US); UNIVERSITE PIERRE ET MARIE CURIE PARIS 6, Paris (FR); INSTITUT CURIE, Paris (FR)

( * ) Notice: Subject to any disclaimer, the term of this patent is extended or adjusted under 35 U.S.C. 154(b) by 0 days.

(21) Appl. No.: 13/147,382

(22) PCT Filed: Feb. 11, 2010

(86) PCT No.: PCT/EP2010/051717
§ 371 (c)(1),
(2), (4) Date: Oct. 14, 2011

(87) PCT Pub. No.: WO2010/092116
PCT Pub. Date: Aug. 19, 2010

(65) Prior Publication Data
US 2012/0052523 A1 Mar. 1, 2012

(30) Foreign Application Priority Data
Feb. 12, 2009 (EP) .................................. 09305127

(51) Int. Cl.
*C12Q 1/02* (2006.01)
*B29C 59/02* (2006.01)
*C12M 1/34* (2006.01)
*G01N 33/50* (2006.01)
(52) U.S. Cl.
CPC ........ *G01N 33/5011* (2013.01); *G01N 33/5005* (2013.01)

(58) Field of Classification Search
CPC .......... G01N 33/5011; G01N 33/5005; G01N 33/54326; G01N 35/0098; B01L 3/5085; B01L 3/5088; B01L 2400/043; B01J 2219/00317; B01J 2219/00655; B01J 2219/00659; B01J 2219/00743; B01J 19/0046; B82Y 5/00; B82Y 30/00; C40B 60/14; C12M 25/08; C12M 21/08; C12M 33/00; C12N 11/06
USPC ........................ 435/288.4, 29, 288.7; 264/293
See application file for complete search history.

(56) References Cited

U.S. PATENT DOCUMENTS 8,652,833 B2 * 2/2014 Morimoto .............. C12M 23/12
427/207.1
2001/0055882 A1 * 12/2001 Ostuni et al. ................... 438/694
(Continued)

FOREIGN PATENT DOCUMENTS

WO WO 2006/111720 10/2006
WO WO 2007/081543 7/2007

OTHER PUBLICATIONS

VerPlank, L. et.al, "Cell cylce-regulated trafficking of Chs2 controls actomyosin ring stability during cytokinesis", May 2005, Mol. Biol. Cell. v. 16(5): 2529-2543.*

(Continued)

*Primary Examiner* — William H Beisner
*Assistant Examiner* — Danielle Henkel
(74) *Attorney, Agent, or Firm* — Saliwanchik, Lloyd & Eisenschenk (57) ABSTRACT

The present invention relates to methods and devices for observing the cell division, in particular the cytokinetic ring, methods for preparing such devices, methods for studying modifications of cell division, and methods for screening compounds of interest which enhance or inhibit cell division.

21 Claims, 7 Drawing Sheets

(56) References Cited

U.S. PATENT DOCUMENTS

| | | | |
|---|---|---|---|
| 2003/0032071 A1* | 2/2003 | Wang et al. ................... | 435/7.21 |
| 2004/0171135 A1* | 9/2004 | Ostuni .................. | B01L 3/5085 |
| | | | 435/283.1 |
| 2005/0264805 A1* | 12/2005 | Cromwell ............ | G01N 21/253 |
| | | | 356/246 |
| 2007/0232703 A1 | 10/2007 | Lee et al. | |
| 2009/0298116 A1* | 12/2009 | Fang ..................... | B01L 3/5085 |
| | | | 435/29 |
| 2011/0003389 A1* | 1/2011 | Nakazawa ............ | B01L 3/5085 |
| | | | 435/383 |
| 2015/0044717 A1 | 2/2015 | Riveline et al. | |
| 2015/0079588 A1 | 3/2015 | Riveline | |

OTHER PUBLICATIONS

Ostuni, E. et al. "Selective Deposition of Proteins and Cells in Arrays of Microwells" *Langmuir*, May 5, 2001, pp. 2828-2834, vol. 17, No. 9.

Yamamura, S. et al. "Single-Cell Microarray for Analyzing Cellular Response", *Analytical Chemistry*, Dec. 15, 2005, pp. 8050-8056, vol. 77, No. 24.

Ochsner, M. et al. "Micro-well arrays for 3D shape control and high resolution analysis of single cells" *Lab on a Chip*, Jun. 21, 2007, pp. 1074-1077, vol. 7.

Mi, Y. et al. "Micromolding of PDMS scaffolds and microwells for tissue culture and cell patterning: A new method of microfabrication by the self-assembled micropatterns of diblock copolymer micelles" *Polymer*, Jun. 28, 2006, pp. 5124-5130, vol. 47, No. 14.

Chang, F. et al. "cdcl2p, a Protein Required for Cytokinesis in Fission Yeast, Is a Component of the Cell Division Ring and Interacts with Profilin" *Journal of Cell Biology*, Apr. 7, 1997, pp. 169-182, vol. 137, No. 1.

Pelham, R. et al. "Actin dynamics in the contractile ring during cytokinesis in fission yeast" *Nature*, Sep. 5, 2002, pp. 82-86, vol. 419.

Written Opinion in International Application No. PCT/EP2010/051717, May 12, 2010, pp. 1-9.

\* cited by examiner

Fig 3B
After curing and removal of stamp

Fig 3C

Fig 3D
After curing and removal of stamp

DEVICES AND METHODS FOR OBSERVING THE CELL DIVISION

CROSS-REFERENCE TO RELATED APPLICATION

This application is the U.S. national stage application of International Patent Application No. PCT/EP2010/051717, filed Feb. 11, 2010, the disclosure of which is hereby incorporated by reference in its entirety, including all figures, tables and amino acid or nucleic acid sequences.

FIELD OF THE INVENTION

The present invention relates to methods and devices for observing the cell division, in particular the cytokinetic ring, methods for preparing such devices, methods for studying modifications of cell division, and methods for screening compounds of interest which enhance or inhibit cell division. It relates to the field of biology, pharmacology and diagnosis.

BACKGROUND OF THE INVENTION

The cytokinetic ring is a fundamental structure which causes the separation of cells at the end of mitosis. Cytokinetic ring dysfunction is a typical target for antitumor agents.

Conserved in prokaryotic and eukaryotic cells, rings are a plane structure of about 200 nm thickness. They are generally observed by fluorescence microscopy, in a plane perpendicular to their closure (Straight et al., 2003; Sun and Margolin, 1998; Wu et al., 2003). This leads to poor spatial and temporal resolutions.

Figure 1A:
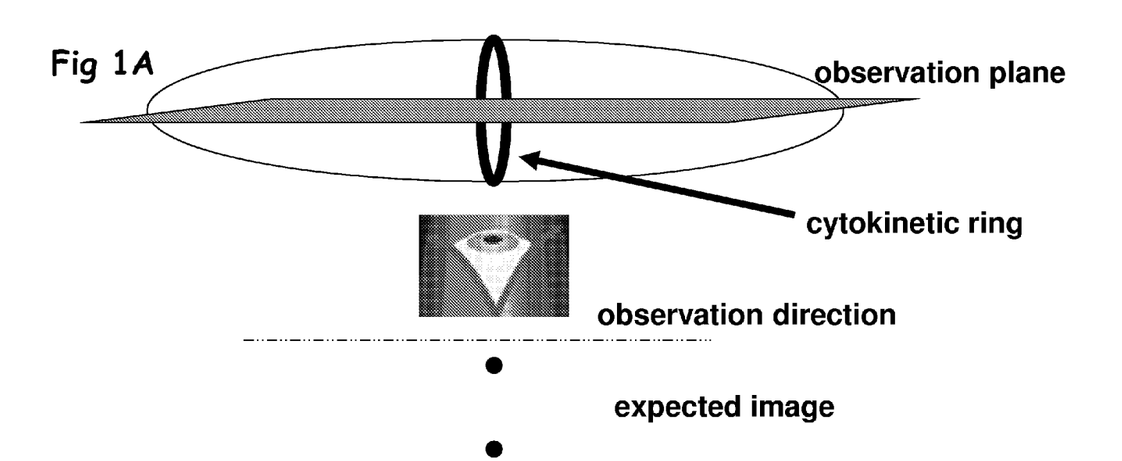
FIG. 1A/The ring is perpendicular to the plane of observation; as a result, only two points of the structure are visualised in the focal (or observation) plane.
Figure 1B:
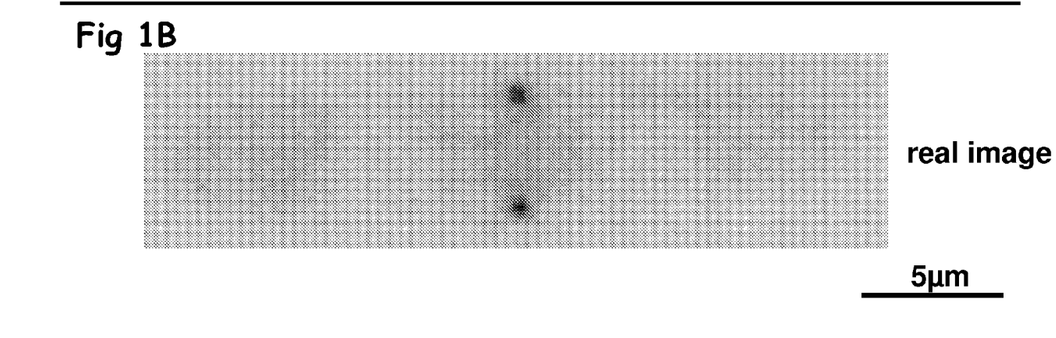
FIG. 1B/The corresponding image of the cytokinetic ring in fission yeast.
Figure 2A:
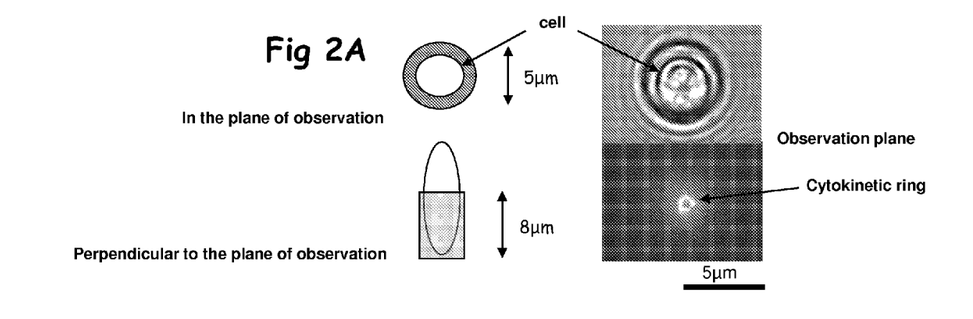
FIG. 2A/The cell is inserted into wells; as a result, the cytokinetic ring is parallel to the observation plane. Cells are grown in these wells that can be prepared either with a filter (FIG. 2B) or with a microfabricated silicon wafer (FIG. 2C); black arrows show the sister cells after ~10 hours growth and division.
Figure 2B:
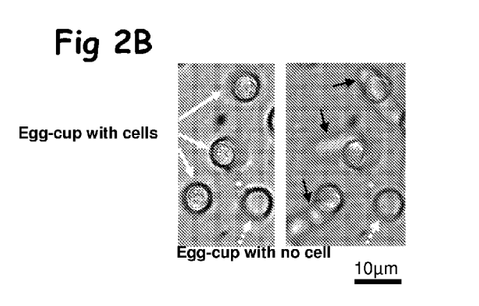
Figure 2C:
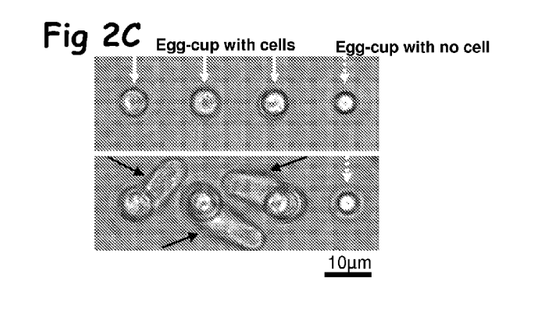
Figure 2D:
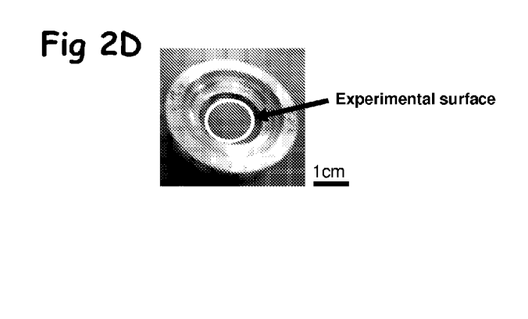
FIG. 2D/The experimental chamber used for the experiments exhibit: up to $10^6$ wells available for observation.
Figure 3A:
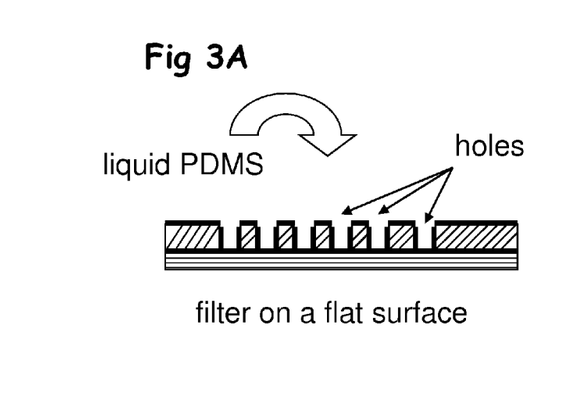
FIG. 3A/Liquid PDMS is poured on a filter glued on a flat surface.
Figure 3B:
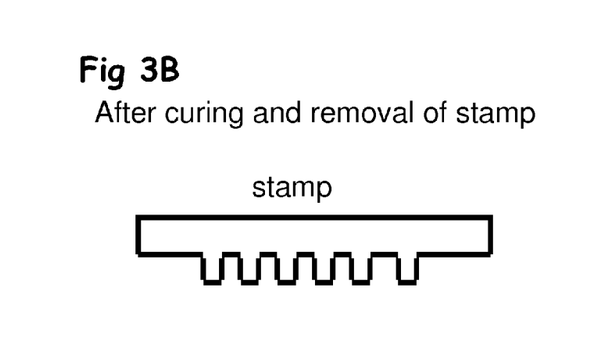
FIG. 3B/after curing, the elastomeric stamp is peeled off the substrate; after silanization, it is applied on a thin layer of liquid PDMS spread on a coverslip (FIG. 3C); after reticulation, the final egg cup surface is achieved after removal of the stamp (FIG. 3D).
Figure 3C:
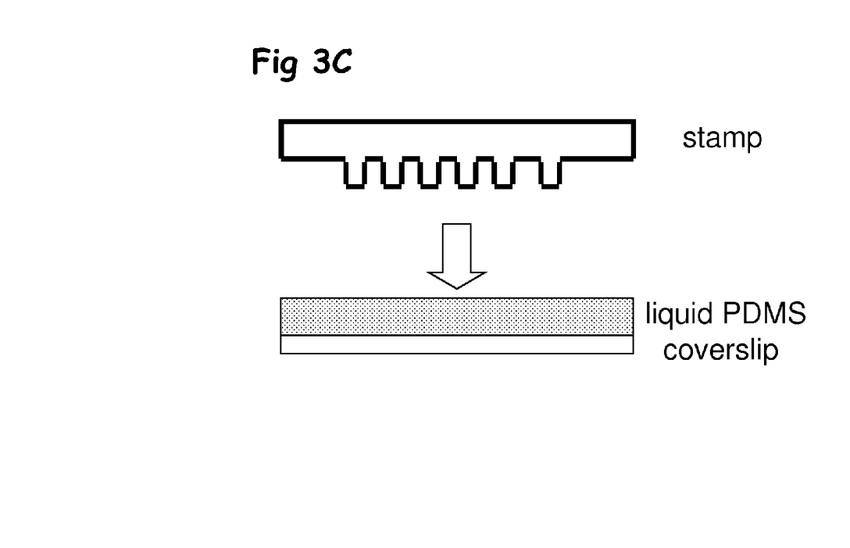
Figure 3D:
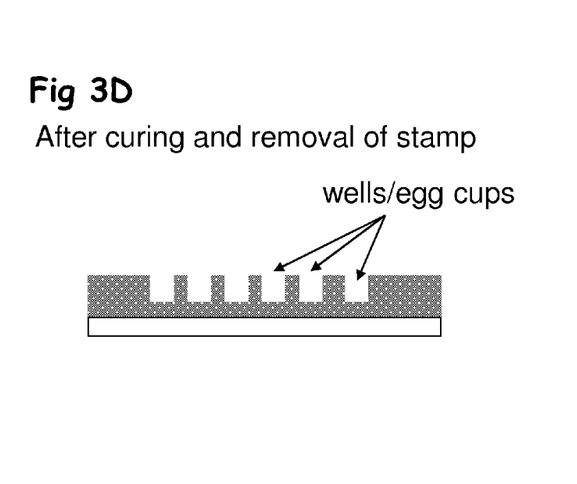

FIG. 1 illustrates the limitations in the approaches used so far. In a single image, the cytokinetic ring appears as two points, because the image results from the intersection between the focal plane and the actual ring. As a result, broken parts of the ring are not visible, and this can lead to misinterpretation in the effect of drugs. One could argue that the entire ring can still be obtained by scanning the ring along the z direction with n images every 400 nm (deconvolution or confocal microscopy). However, this way of acquiring is not efficient: i/photobleaching due to overexposure of the ring damages the signal and the cell viability; ii/with this method, the acquisition of a single ring requires n times longer than a single plane acquisition, thus reducing the time resolution.

Accordingly, due to the interest of cytokinetic ring, there is a strong need to provide devices and methods allowing to overcome these drawbacks.

Arrays of microwells suitable for cell culture of individual cells have already been disclosed. However, none of them is appropriate to overcome the above-detailed drawbacks for the observation of the cytokinetic ring. As a non-exhaustive illustration, the following articles can be cited.

Ostuni et al (2001, *Langmuir*, 17, 2828-2834) discloses arrays of microwells, each well being suitable for attaching one cell. The wells have a diameter of less than 100 μm (e.g., 50 and 25 μm) and a depth of less than 50 μm (e.g., 1.3, 5 or 50 μm). The surface within the wells is coated by fibronectin.

Yamamura et al (2005, *Analytical Chemistry*, 77, 8050-8056) discloses a single-cell microarray and its use for screening. The microchambers are a cylinder having 10-μm width, 12-μm depth and 30-μm pitch.

Ochsner et al (2007, *Lab on a Chip*, 7, 1074-1077) discloses a device for 3D shape control of single cells. The microwells are coated with fibronectin. The wells' depth is 10 μm and the lateral dimensions were from 81 μm$^2$ to 900 μm$^2$. The 3D shape is controlled by the form of the wells (square, circle, triangles, rectangles, spindles).

Mi et al (2006, *Polymer*, 47, 5124-5130) discloses a new method of microfabrication of microwells. The microwells can be adapted to contain a single cell.

However, the devices disclosed in these articles imply optical resolution which could be significantly improved, allowing thereby optimal observation quality of key cellular organelles. In addition, none of these documents comprises any teaching about the cytokinetic ring, in particular the orientation of the closure plane thereof.

SUMMARY OF THE INVENTION

For the first time, the inventors provide devices and methods allowing the observation of the whole cytokinetic ring in the unique plane of closure. Until now, nobody had the idea to place cells in conditions such that they all present a cytokinetic ring in the same orientation, more particularly in an orientation allowing the observation of a high number of cells promptly with accuracy.

Accordingly, the present invention concerns a device for observing the cytokinetic ring of cells, wherein the device comprises a support and a microfabricated substrate bearing a plurality of wells, each one containing a unique cell, and, characterized in that the wells have a structure suitable for orienting the closure plane of the cytokinetic ring parallel of said cells to the observation plane.

Preferably, the width of wells is about the diameter for round cells or about the short axis of the cell for cells which have oval or rod form. Preferably, the width of wells is smaller than or equal to the depth of wells.

Preferably, the support is a plate of glass, preferably a silanised glass, more preferably a silanised glass coverslip. However, a quartz coverslip is also considered because it allows a high resolution. Preferably, the microfabricated substrate is made of poly(dimethylsiloxane) (PDMS). In a preferred embodiment, the thickness of the support and the microfabricated substrate is less than 200 μm, preferably less than 150 μm, more preferably between 100 and 150 μm. Optionally, the device further comprises physical barriers separating several groups of wells from each other on the device. In addition, such a device can further comprise microfluidic system in order to address different samples or media to the groups of wells on the device.

In a first embodiment, the cells have a cell wall and the depth of wells is at least or about ½ of the cell diameter or long axis.

In a particular embodiment, the cells are yeast, the well width is between 1 to 6 μm, preferably between 3 to 5 μm, and the well depth is between 4 to 10 μm, preferably between 6 to 8 μm. In another particular embodiment, the cells are bacteria and the well width can be comprised between 500 nm and 3 μm.

In a second embodiment, the cells are devoid of cell wall and the device further comprises a top covering the wells, the wells depth being such that the cells are entirely contained into them (i.e., about a cell length for the depth), and the bottom of the wells and the top being coated by molecules that promote cell adhesion. Preferably, the molecules that promote cell adhesion are fibronectin. In a preferred embodiment, the wells depth and width are about 10-50 μm, preferably about 12-20 μm.

The present invention concerns a method for observing the cytokinetic ring of cells comprising a) providing a device according to the present invention bearing the cells; and b) observing the cytokinetic ring with the closure plane of the cytokinetic ring parallel to the observation plane. It also concerns the use of a device according to the present invention for observing the cytokinetic ring of cells with the closure plane of the cytokinetic ring parallel to the observation plane.

The present invention further concerns the use of a device according to the present invention for screening or identifying test molecules able to modulate the cell division. In particular, the present invention concerns a method for screening or identifying test molecules able to modulate the cell division comprising:

providing a device according to the present invention bearing cells which have been contacted with a test molecule;
assessing the closure of the cytokinetic ring of the cells;
comparing the closure of the cytokinetic ring of the cells in presence and in absence of the test molecule; and,
selecting the test molecule for which the closure is significantly different in presence and in absence of the test molecule, thereby identifying a test molecule able to modulate the cell division.

Finally, the present invention concerns the use of a filter having a suitable pore diameter and thickness for preparing a device according to the present invention. In particular, the present invention concerns a method for preparing a device according to the present invention comprising:

providing a filter having a suitable pore diameter and thickness;
putting the filter on a first support such as the bottom side of the pores is closed;
pouring a liquid polymer that might be hardened and after hardening;
peeling off the obtained replica from the filter, thereby providing a template;
optionally, carrying out an anti-adhesive treatment on the template to facilitate the demolding;
spreading another liquid polymer that might be hardened onto a second support;
gently pressing or placing the template against the second support coated with the polymer and, after polymer hardening;
removing the template from the obtained microfabricated substrate, thereby obtaining the device.

In another embodiment and in the context of cells with a cell wall and having an oval or rod shape, the devices according to the invention are also useful to observe any plane perpendicular to the long axis of the cells. Therefore, the present invention also concerns a method for observing a plane perpendicular to a long axis of cells with cell wall and having an oval or rod shape, comprising a) providing a device according to the present invention bearing the cells; and b) observing the plane parallel to the observation plane. The present invention further concerns the use of a device according to the present invention for observing a plane perpendicular to a long axis of cells with cell wall and having an oval or rod shape with a parallel arrangement to the observation plane. In a preferred embodiment, the observed perpendicular plane is the tip of the cells. In addition, the present invention concerns the use of a device according to the present invention for screening or identifying a test molecule able to modulate the tip growth of cells with cell wall and having an oval or rod shape. More specifically, it concerns a method for screening or identifying a test molecule able to modulate the tip growth of cells with cell wall and having an oval or rod shape comprising:

providing a device according to the present invention bearing cells which have been contacted with a test molecule;
observing the tip growth of the cells;
comparing the tip growth of the cells in presence and in absence of the test molecule; and,
selecting the test molecule for which the tip growth is significantly different in presence and in absence of the test molecule, thereby identifying a test molecule able to modulate the tip growth.

BRIEF DESCRIPTION OF THE DRAWINGS

FIG. 1: The common set-up for observing the cytokinetic ring.

FIG. 2: The experimental set-up.

FIG. 3: Method for preparing the egg cup surface using the filter.

FIG. 4: Cytokinetic ring closure in a unique plane.

FIG. 5: Specific drugs stop the closure.

FIG. 6: The closure velocity is constant and depends on the temperature. After image treatment, the diameter is plotted as a function of time. As shown, the decrease in diameter is linear with time within our resolution, yielding a closing velocity of 95 nm/min at 27° C. This velocity increases with the temperature from 15 nm/min at 18° C. up to 130 nm/min at 36° C. These values are consistent with the expected temperature dependence for the ring dynamics. (Pelham and Chang, 2002; Wu et al., 2003).

FIG. 7: Illustrative embodiment of the devices. (1) refers to the microfabricated substrate, preferably made of PDMS or gel; (2) refers to a glass coverslip; (3) refers to a dialysis membrane or a microfabricated substrate with holes allowing permeability to medium; (4) refers to a spacer. By "objective" is intended microscope objective.

DESCRIPTION OF THE INVENTION

In the present invention, the inventors provide devices and methods allowing the observation of the whole ring in the unique plane of closure. In particular, the devices of the invention allow an orientation of the closure plane of the cytokinetic ring parallel to the observation plane due to the appropriate form and coating of wells and a good optical resolution (i.e., objective with high numerical aperture, larger than 1.3) due to a thickness of the device of less than 200 µm. Accordingly, a high number of cells can be observed rapidly and easily with accuracy. The approach is also cheap and allows an automated observation. For instance, more than 1,000 rings can be observed in about one hour.

The inventors illustrate this new method by observing the closure of the cytokinetic ring with the fission yeast *Schizosaccharomyces pombe* (*S. pombe*, see FIG. 1 and FIG. 2). At this stage, their approach allows the observation of up to $10^6$ cells in one hour in an automated manner. The same method can be extended to any cell type—prokaryotic and eukaryotic—by adjusting the shape and the coating of the microfabricated substrates (Weibel et al., 2007) and paves the way towards large throughput screenings for antibacterial/anticancer drugs (Jackson et al., 2007; Lang et al., 2006) and cancer diagnosis (Mathon and Lloyd, 2001).

Accordingly, the present invention concerns a device comprising a support and a microfabricated substrate bearing a plurality of wells suitable for containing a unique cell and for orienting the closure plane of the ring parallel to the observation plane.

Figure 7A:
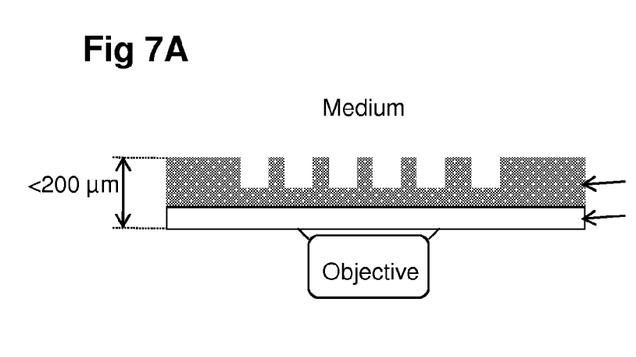
In FIG. 7A, the device comprises a support consisting in a glass coverslip as thin as possible and a micro fabricated substrate placed on the support. The medium can be added under the microfabricated substrate. Thereby, the nutrients are accessible from the upper side of the wells.
Figure 7B:
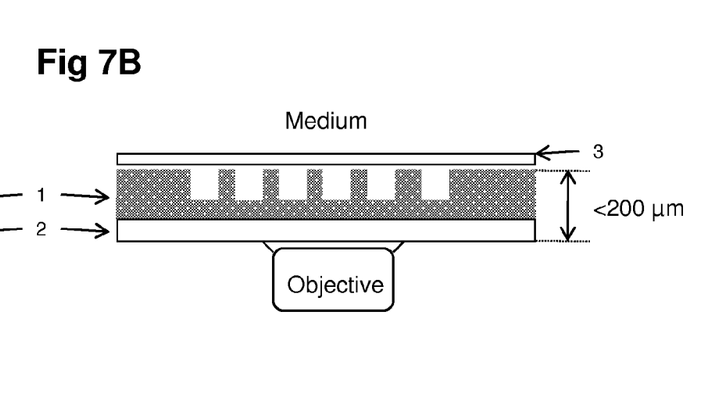
In FIG. 7B, the device comprises a support consisting in a glass coverslip as thin as possible, a microfabricated substrate placed on the support and in addition an upper surface made of a material permeable to medium such as a dialysis membrane or a microfabricated substrate with holes. The nutrients enter from the top through the dialysis membrane or microfabricated substrate.
Figure 7C:
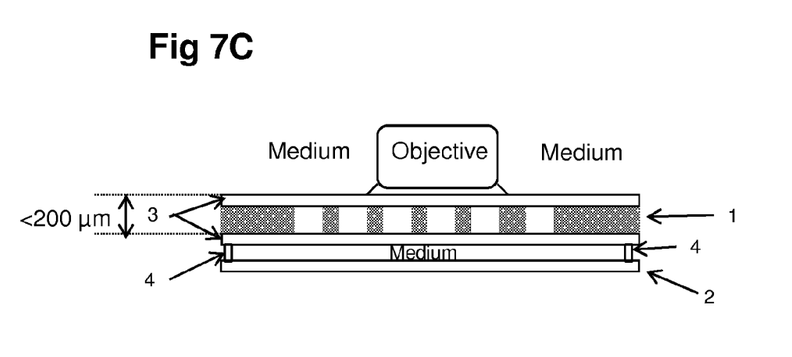
In FIG. 7C, the device comprises a microfabricated substrate with wells going through the microfabricated substrate. This microfabricated substrate with wells is sandwiched between two dialysis membranes or microfabricated substrates with holes allowing permeability to medium. Then, the whole lies on a glass coverslip with medium between the coverslip and the bottom dialysis membrane or microfabricated substrate with holes. The nutrients provided by medium enter from both sides (top and bottom). In this embodiment, the objective is placed at the upper side to benefit to the shortest working distance. In case the microfabricated substrate is made of gel, the nutrient can also enter through the sides all around the wells.

Preferably, the microfabricated substrate comprises a high number of wells, e.g., at least or about 10, 20, 50, 100, 150, 200, 300, 400, 500, 1,000, 5,000, 10,000, 50,000, 100,000, 500,000, or 1,000,000 wells. For instance, the support comprises between 100 and 4,000,000 wells per cm² of substrate, preferably between 500,000 and 4,000,000 wells by cm² of substrate, more preferably between 1,000,000 and 4,000,000 wells by cm² of substrate. The wells are sufficiently separated to be discriminated during microscopy observation. In a particular embodiment, the wells are spaced of at least 200 nm, preferably by about 200 nm, 500 nm, 1 µm, 5 µm, or 10 µm. The space between the wells can optionally be treated with a cytophobic material (i.e., preventing cell adhesion), for instance polyethyleneglycol (PEG). The wells of the microfabricated substrate can have a bottom made of the microfabricated substrate (see for example, FIG. 3) or can go through the microfabricated substrate (i.e., the bottom of the well is the support, for example see FIG. 7C).

By "microfabricated substrate" is intended a microfabricated solid surface including, e.g., silicon, functionalized glass, germanium, ceramic, a semiconductor material, PTFE, carbon, polycarbonate, mica, mylar, plastic, quartz, polystyrene, gallium arsenide, gold, silver, metal, metal alloy, fabric, and combinations thereof. In particular, the microfabricated substrate is made of a solid material preferably biocompatible or with a surface treatment that makes it biocompatible. The following materials can be used for microfabrication: a polymer that can be crosslinked (PDMS, agar, polyacrylamide (PAA) . . . ), a glassy material (polycarbonate (PC), polystyrene (PS) . . . ), a metal or a semiconductor material.

By "for containing a unique cell" is intended that the well is suitable for containing one and only one cell.

By "for orienting the closure plane of the ring parallel to the observation plane" is intended that the structure of the well is adapted to obtain the suitable orientation of the cytokinetic ring. In a first aspect of the well structure, the width and the depth of the wells are adapted to obtain the suitable orientation of the cytokinetic ring. In a second aspect of the well structure, the cell attachment points are adapted to obtain the suitable orientation of the cytokinetic ring. By "the closure plane of the ring parallel to the observation plane" is intended that the closure plane of the cytokinetic ring is parallel to the support. The observation or focal plane is defined herein, where the structure of interest, i.e. the ring, appears entirely on the image (see FIG. 1 and FIG. 2). The direction along the wells/egg cups depth is perpendicular to this plane.

By the term "about" is intended to mean the value more or less 5% thereof. When the term "about" is used for defining the width of the well for cells with a cell wall, then it means the value with optionally 5% more.

For cells rather round, one can define a mean diameter which is the diameter of cells before adhesion to the surfaces. For cells which have oval or rod shape, one can define a short axis and a long axis.

For cells having a cell wall, generally having oval or rod shape, the cytokinetic ring is always perpendicular to the long axis. Accordingly, the orientation of the cytokinetic ring can easily be controlled through the appropriate orientation of cells in the device. Hence, cells have to be placed so that the long axis is perpendicular to the support. The same set-up will work also for spherical cells with walls such as *S. cerevisiae*, since they elongate during growth. There is no need of cell attachment molecules in the wells.

For cells devoid of cell wall, the orientation of the cytokinetic ring can be controlled through the cell attachment points. Indeed, in case of two opposite points of attachment, the cytokinetic ring is perpendicular to the axis joining the two opposite attachment points. Accordingly, to be perpendicular to the support, the two opposite attachment points have to be at the bottom and the upper surfaces of the wells. Obviously, the wells do not include any other substantial attachment points. Therefore, the device further comprises in this case a top covering the wells. Accordingly, in a particular embodiment dedicated for cells devoid of cell wall, the device comprises a support and a micro fabricated substrate bearing a plurality of wells suitable for containing a unique cell, characterized in that the bottom of the wells is coated with cell adhesive materials and the lateral sides thereof are non-adhesive and in that the device further comprise an upper surface under the wells coated with cell adhesive materials. The one skilled in the art knows how to adapt the device and the method for preparing it in the appropriate way. For instance, in order to prepare the corresponding substrates, standard microfabrication methods could be used. For example, a dialysis membrane could be coated with fibronectin; the filter could be glued onto this substrate, thus forming the expected egg-cups; an upper membrane coated with fibronectin would be pressed on top of them after deposition of cells.

In general, the width or diameter of each well for round cells is at least the mean diameter of cells but far less than two mean diameters; and the width of each well for cells which have oval or rod form is at least the short axis of the cell but far less than the long axis. The width of each well is as precisely as possible the mean diameter or the short axis of the cell. Preferably, the width of each well is the diameter or the short axis of the cell more or less 1, 2, 5, 10, 20 or 30% of the diameter or the short axis. Indeed, if elastic materials are used for the microfabricated substrate, an isotropic deformation or strain would be applied on the substrate to enlarge the well diameter, while the cells would be placed into wells; the deformation or strain would be then released; as a result, cells would be strongly held in place, like in a vice.

The depth of each well is such that it prevents the cell to move away when subjected to an external flow, and it orients the closure plane parallel to the observation plane. In a preferred embodiment, the depth of each well is preferably at least or about ⅓ of the cell diameter or long axis, preferably at least or about ½. By "at least or about" is intended at least ⅓ or ½ of the cell diameter or long axis or ⅓ or ½ of the cell diameter or long axis more or less 5% thereof. For instance, it can be comprised between ½ of the cell diameter or long axis and the full cell diameter or long axis. The depth of each well can also be almost or about the cell diameter or long axis, thereby the whole cell is contained into the well. This latter case is particularly preferred for cells devoid of cell wall, like mammalian cells. However, for cells with cell wall such as bacteria or fungi (e.g., yeast), a well depth between ½ and ¾ of the cell diameter or long axis is preferred.

The cell suitable for being used with the device of the present invention can be any eukaryotic or prokaryotic cell. In particular, prokaryotic cells can be bacteria and eukaryotic cells can be a fungal cell such as yeast, animal, mammalian, human, or plant cells. Cell can be for example fibroblast, hematopoietic, endothelial and epithelial cell. Cell can be derived from a healthy or pathologic tissue or organism. The cell can be wild type or modified/recombinant cells. In a particular embodiment, the mammalian cell can be a tumor cell.

In the case of cells devoid of cell wall such as mammalian cells, the width of the well can be for instance about 10-50 µm, preferably about 12-20 µm. In addition, the bottom of the well is coated by molecules that promote cell attachment. These molecules are well known to those of ordinary skilled in the art and comprise antigens, antibodies, cell adhesion molecules (like cadherins for example), extracellular matrix molecules such as laminin, fibronectin, synthetic peptides, carbohydrates and the like, more preferably fibronectin. In addition, the wells depth is such that the cells are entirely contained into them (i.e., about a cell diameter for the depth) and the wells are covered by a top coated by molecules that promote cell attachment. For instance, the wells depth can be about 10-50 µm, preferably about 12-20 µm. The two cell attachment sites at the bottom and the upper surfaces of the wells allow the appropriate orientation of the closure plane of the ring. In this case, the device of the invention comprises a support bearing at least two wells suitable for containing a unique cell and a top covering at least two wells, the bottom of the wells and the top being coated by molecules that promote cell attachment and the sides are preferably treated with a cytophobic (or cell anti adhesive) material.

In the case of bacteria or yeast, in a preferred embodiment, the wells width is the cell diameter or the short axis more or less 1, 2, 5, 10, 20 or 30% of the diameter or the short axis, and the depth is preferably one third to one of the long axis, more preferably one third to one half. In case of bacteria having generally a short axis comprised between 0.5 and 3 µm, the well width can be comprised between 500 nm and 3 µm. The long axis of bacteria is highly variable among bacteria. However, for instance, a depth of 1, 2, 3, 5, 7 or 10 µm can be appropriate. In particular for E. coli, the well width can be 800 mu and the depth can be 2 µm. In case of yeast, the well width is between 1 to 6 µm, preferably between 3 to 5 µm, and the well depth is between 4 to 10 µm, preferably between 6 to 8µm. Wells with those features are adapted for most of the yeast. Preferably, the well width is smaller than or equal to the well depth. In case of fission yeast, the well width can be 5 µm and the depth can be 8 µm. For bacterial and fungal cells, more generally for cells having a cell wall, the top is not necessary, even more rather undesirable. Indeed, the closure plane of the ring is always perpendicular to the long axis of the cells. Accordingly, an appropriate placement of the cells is sufficient to obtain the desired orientation of the closure plane of the ring.

The well size (i.e., width and depth) can be adapted easily by the man skilled in the art for each specific cell to study.

The support has to be convenient for confocal, optical and/or fluorescence microscopies. An appropriate support can be any flat substrate promoting a good adhesion with the polymer used for the microstructure. In a more preferred embodiment, the support comprises or is a plate of glass. For example, a convenient plate according to the present invention is a coverslip or a slide. In a preferred embodiment, the coverslip is as thin as possible. For instance, the thickness of 0.085 to 0.13 mm is convenient. In an alternative preferred embodiment, the support comprises or is a dialysis sheet, such as a cellulose membrane (Sigma, MWCO 12-14,000), or any membrane allowing medium exchange between compartments. In another alternative preferred embodiment, the support comprises or is a micro fabricated substance, optionally with holes with a diameter far less than the well width (e.g., less than 10, 20, 30, 40 or 50% of well width). The size of the holes is enough to allow the permeability to the medium (by medium is intended a medium appropriate for cell culture).

In addition, when a top is necessary, a convenient top can be for instance a dialysis sheet, such as a cellulose membrane (Sigma, MWCO 12-14,000), or any membrane allowing medium exchange between compartments. Alternatively, the top can also be micro fabricated, optionally with holes as defined above.

Microfabrication techniques for preparing micro fabricated substrates are well-known by the man skilled in the art.

For instance, microfabrication techniques for preparing the stamp used to produce the micro fabricated substrate of the device can be for instance photolithography, thin-film deposition, wet chemical etching, reactive ion etching, inductively coupled plasma deep silicon etching, laser ablation, air abrasion techniques, and other techniques. Polymeric substrate materials are preferred for their ease of manufacture, low cost and disposability, as well as their general inertness. The polymeric substrate materials are preferably cross-linkable. They can be biocompatible and have a weak adhesion for cells. In a preferred embodiment, the substrate material is made of PDMS. Techniques are disclosed for instance in the following patents U.S. Pat. Nos. 6,753,131; 6,516,168 and 6,143,412.

The substrate materials for the stamp can comprise the following polymeric materials without to be limited thereto:
  glassy polymers, such as polystyrene, polymethylmethacrylate (PMMA), polycarbonate, polytetrafluoroethylene (TEFLON®), polyvinylchloride (PVC);
  elastomeric materials polydimethylsiloxane (PDMS), polybutadiene, polyurethane, and the like;
  gels (agar, PAA . . . ) and the like.

The microfabricated substrates of the device are readily manufactured from masters, using well-known molding techniques, such as injection molding, hot embossing or by molding a polymer that might be crosslinked (soft lithography).

The substrate materials for the microfabricated substrates of the device can be the same than stamps and can comprise the following polymeric materials without to be limited thereto:
- glassy polymers, such as polystyrene, polymethylmethacrylate (PMMA), polycarbonate, polytetrafluoroethylene (TEFLON®), polyvinylchloride (PVC);
- elastomeric materials polydimethylsiloxane (PDMS), polybutadiene, polyurethane, and the like;
- gels (agar, PAA . . . ) and the like, with the advantage of allowing the diffusion of nutrients within the microfabricated structure and therefore the nutrients can diffuse through the side all around the wells.

In a preferred embodiment, the microfabricated substrate is made of biocompatible materials and has a weak adherence for cells. In a most preferred embodiment, the micro fabricated substrate is made of PDMS. In a second preferred embodiment, the microfabricated substrate is made of gel including agar, PAA (poly acrylamide) and the like.

In the present invention, the inventors provide an original and real cheap method for preparing the micro fabricated substrates. Indeed, they use filters to prepare a stamp for preparing suitable wells. In particular, filters are chosen so as to present pore diameter corresponding to the wells width. In addition, filters are also chosen so as to present a thickness corresponding to the wells depth. For instance, the filters can be those commercialized by Millipore (Isopore) in polycarbonate or by GE Osmonics Labstore Poretics in polycarbonate or polyester. In those products, the manufacturing process of the membrane ensures a precise pore diameter and a consistent pore size. For instance, filters commercialized by Millipore (Isopore) or by GE Osmonics Labstore Poretics are available with the following pore size: 0.08, 0.1, 0.2, 0.4, 0.6, 0.8, 1, 1.2, 2, 3, 5, 8, 10, 12 and 14 µm. Preferably, the filters thickness is comprised between 5 and 25 µm. If larger pore diameter is necessary, other commercially available filters with larger pore diameter can be used.

In a particular embodiment, the present invention concerns a method for preparing a device according to the present invention comprising:
- providing a filter having a suitable pore diameter and thickness;
- putting the filter on a first support such as the bottom side of the pores is closed;
- pouring a liquid polymer that might be hardened and after hardening;
- peeling off the obtained replica from the filter, thereby providing a template;
- optionally, carrying out an anti-adhesive treatment on the template to facilitate the demolding;
- spreading another liquid polymer that might be hardened onto a second support;
- gently pressing or placing the template against the second support coated with the polymer and, after polymer hardening;
- removing the template from the obtained microfabricated substrate, thereby obtaining the device.

In a particular embodiment, the filter having a suitable pore diameter and thickness is a filter with a pore size comprised between 0.08 and 50 µm, preferably between 0.08 and 20 µm, still more preferably between 0.08 and 15 µm, and a thickness comprised between 5 and 25 µm. The filter is generally a polycarbonate or polyester filter. In an embodiment, if necessary, the method further comprises a step of coating the device with a thin layer that makes it biocompatible.

Preferably, the liquid polymer can be hardened after crosslinking or cooling below the glassy transition. Preferably, if the materials for the stamp and the microfabricated substrate are the same, the method further comprises a step of silanization after detaching the obtained stamp from the filter and before spreading a biocompatible polymer with a weak cell-adhesion onto a second support. Preferably, the biocompatible polymer with a weak cell-adhesion is a siloxane-based polymer. In a most preferred embodiment, the microfabricated substrate is PDMS. In a particular embodiment, the cross-linkable polymer and the bio compatible polymer are both a siloxane-based polymer, more preferably PDMS.

For instance, a method is described in detail in the example section. However, the devices of the invention are not limited to those obtained by this method. The man skilled in the art can adapt several methods to prepare such devices.

Preferably, the resulting microfabricated substrate has for instance a thickness of about 20-100 µm, preferably about 30-50 µm. Preferably, the siloxane-based polymer is PDMS. Preferably, the support is a glass coverslip, more preferably as thin as possible.

Due to the working distance and the resolution needed to observe the cytokinetic ring, the thickness of the support and the microfabricated substrate need to be as thin as possible. Indeed, objective with high numerical aperture 1.3-1.65 are required, and therefore they have to close to the object of observation. Accordingly, the thickness is preferably less than 200 µm, more preferably less than 150 µm, still more preferably between 100 and 150 µm.

Accordingly, in a first particular preferred embodiment, the device comprises a support and a micro fabricated substrate bearing a plurality of wells suitable for containing a unique cell as defined above. The support is preferably a glass coverslip. The micro fabricated substrate is supported by the coverslip. The micro fabricated substrate is for instance PDMS substrate or gel. The nutrients can be added by the upper side of the wells. The objective is placed close to the glass coverslip. An illustrating scheme is provided in FIG. 7A.

In a second particular preferred embodiment, the device comprises a support, a microfabricated substrate bearing a plurality of wells suitable for containing a unique cell as defined above, and a top. The support is preferably a glass coverslip. The microfabricated substrate is supported by the coverslip. The microfabricated substrate is for instance PDMS substrate or gel. The top can be a dialysis membrane or a microfabricated substrate, optionally having little holes allowing it to be permeable to medium. For instance, the holes have a diameter of less than 0.05 or 1 µm. The nutrients can be added by the upper side of the wells. The objective is placed close to the glass coverslip. An illustrating scheme is provided in FIG. 7B.

In a third particular preferred embodiment, the device comprises a microfabricated substrate with wells going through the microfabricated substrate. This microfabricated substrate with wells is sandwiched between two dialysis membranes or microfabricated substrates with holes allowing permeability to medium, and then is supported by a glass coverslip with medium between the coverslip and the bottom dialysis membrane or microfabricated substrate. The nutrients provided by medium enter from both sides (top and bottom). In this embodiment, the objective is placed at the upper side to benefit to the shortest working distance. An illustrating scheme is provided in FIG. 7C.

The device of the present invention is useful for studying the cytokinetic ring. The cytokinetic ring can be observed by microscopy, in particular fluorescence microscopy. Generally, the cytokinetic ring is observed through fluorescent proteins (Glotzer M, Science. 2005 Mar. 18; 307(5716):1735-9).

The fluorescent proteins can be any protein of the cytokinetic ring. For instance for fission yeast, the fluorescently labelled protein (e.g., by YFP, GFP, EGFP, mCherry and the like) can be myosin (e.g., myosin II regulatory light chain such as RLC1-mCherry, or myosin II heavy chain such as myo2-YFP), paxillin-like protein Pxl1 (such as pxl1-GFP), membrane-cytoskeletal interactions (e.g., F-BAR domains such as cdc15-YFP), 1,3-beta-glucan synthase (e.g., catalytic subunit Bgs1 such as bgs1-GFP) and the like. Other proteins suitable are disclosed in the articles of Wu and Pollard (Wu et al, Methods Cell Biol. 2008; 89:253-73; Vavylonis et al, Science. 2008 Jan. 4; 319(5859):97-100; Wu et al, J Cell Biol. 2006 Jul. 31; 174(3):391-402; Wu and Pollard, Science. 2005 Oct. 14; 310(5746):310-4.; Kovar et al, Mol Biol Cell. 2005 May; 16(5):2313-24; Wu et al, Dev Cell. 2003 November; 5(5):723-34), and their homologs in other cells will be appropriate. In case of fluorescently labelled proteins, the cells are genetically engineered in order to express such fluorescently labelled proteins. Alternatively, the ring can be observed by using fluorescently labelled ring marker or antibody directed against any protein of the ring. For instance, rhodamine or Alexa-phalloidine is suitable for this use, as well as immunofluorescence staining with anti-myosin antibodies (Glotzer M, *Science*. 2005 Mar. 18; 307(5716):1735-9).

In addition to basic research, two other types of application can be envisioned for the devices of the invention. The first use is the screening of molecules of interest. Therefore, the present invention concerns the use of the device of the present invention for molecules screening. The second use is the diagnosis. Therefore, the present invention concerns the use of the device of the present invention for proliferative disease diagnosis, in particular tumor or cancer diagnosis.

The present invention concerns a method for observing the cytokinetic ring of cells comprising a) providing a device according to the present invention bearing the cells; and b) observing the cytokinetic ring with the closure plane of the cytokinetic ring parallel to the observation plane. In particular, the step a) comprises providing the cells for which the cytokinetic ring has to be observed; selecting a device according to the present invention adapted for the provided cells and placing the cells on the device. It also concerns the use of a device according to the invention for observing the cytokinetic ring of cells with the closure plane of the cytokinetic ring parallel to the observation plane.

In the first use, the device of the present invention is used to assay or test the ability of a test molecule to modulate the cell division, in particular to assay or test the ability of a test molecule to modulate the closure of the ring. In particular, a molecule of interest is a molecule able to block or inhibit the cell division, in particular through the blockage or inhibition of the closure of the cytokinetic ring. Accordingly, the present invention concerns a method for screening or identifying a test molecule able to modulate the cell division comprising:

providing a device according to the present invention bearing cells which have been contacted with a test molecule;

assessing the closure of the ring of the cells;

comparing the closure of the ring of the cells in presence and in absence of the test molecule; and, selecting the test molecule for which the closure is significantly different in presence and in absence of the test molecule, thereby identifying a test molecule able to modulate the cell division.

In particular, the step a) comprises providing cells on which the test molecule has to be tested; selecting a device according to the present invention adapted for the provided cells and placing the cells on the device.

In a first embodiment, the cells are contacting with the test molecule before being placed on the devices of the invention. Accordingly, the method can comprise previous steps of contacting cells with the test molecule and loading the contacted cells on the device. In an alternative embodiment, the cells are contacting with the test molecule when they are already placed on the devices of the invention. According, the method can comprise previous steps of loading the cells on the device of the present invention and contacting cells with the test molecule.

The cells can be placed into the wells of the device by any means known in the art. For instance, the cells can be introduced in it by centrifugation, preferably followed by washing steps. Alternatively, cells could be loaded by filtering the cells sample through the membrane, prior its attachment to a glass substrate; this procedure would be followed by washing steps.

In a first embodiment, the step of assessing the closure of the ring comprises the measure of the number of cells having an open ring and of the cells having a closed ring. In this embodiment, the closure is significantly different in presence and in absence of the test molecule when the number of open and closed ring is significantly different in presence and in absence of the test molecule. In a second embodiment, the step of assessing the closure of the ring comprises the measure of the velocity of the ring closure. In this embodiment, the closure is significantly different in presence and in absence of the test molecule when the velocity is significantly different in presence and in absence of the test molecule. In a third embodiment, the step of assessing the closure of the ring comprises both the measure of the number of cells having an opened ring and of the cells having a closed ring and the measure of the velocity of the ring closure. In a fourth embodiment, the step of assessing the closure of the ring comprises registering the cytokinetic ring for several cells either in presence or in absence of the test molecule. By "several" is preferably intended at least 100, 1,000, 10,000, 100,000 or 1,000,000 cells in each condition. If the test molecule does not modulate the cell division, the ring of cells can statistically have any position. The superposition of the registered rings results in a disk. Alternatively, if the test molecule blocks or inhibits the ring closure, the ring of cells has a higher probability to be opened. The superposition of the registered rings results in a circle. Therefore, a test molecule blocking or inhibiting the ring closure can be selected through the form for the superposition of the registered rings.

The cells can be synchronized at the beginning of the method or not.

When the cells are prokaryotic, the identified molecules have an interest as antibiotic agents and the method is a method for screening or identifying a test molecule having antibiotic property. When the cells are eukaryotic, the identified molecules have an interest as anti-proliferative agents and the method is a method for screening or identifying a test molecule having anti-proliferative property, in particular anti-tumor property. When the cells are fungi, the identified molecules have an interest as anti-fungal agents and the approach is a method for screening or identifying a test molecule having anti-fungal property.

The test molecule may be of various origin, nature and composition. It may be any organic or inorganic substance, such as a lipid, peptide, polypeptide, nucleic acid, small molecule, etc., isolated or mixed with other substances. For instance, the test compound can be an antibody, an antisense oligonucleotide, or an RNAi. The molecule may be all or part of a combinatorial library of products, for instance.

The advantage of the device of the present invention is that a high number of test molecules can be simultaneously assayed due to the high number of wells and the automated record of the ring closure. In this embodiment, the device according to the present invention can comprise several groups of wells on the same plate separated from each other such that each group can be incubated in a different medium. For instance, a group of wells can be contacted with a test molecule and another group can be contacted with another test molecule or without any test molecule. This separation can be provided by a physical barrier such as teflon seal or directly PDMS molded separations. For example, see SPI Teflon® of SPI Supplies, Teflon® Printed Slides of Aname. For instance, each group of wells can comprise at least or about 100, 1,000, 10,000, 100,000 or 1,000,000 wells. Microfluidic system can be further used in order to address a different drug at different locations or groups of wells on the device (Melin J, Quake S R., Annu Rev Biophys Biomol Struct. 2007; 36:213-31; Hansen C, Quake S R, Curr Opin Struct Biol. 2003 October; 13(5):538-44; Hong J W, Quake S R, Nat Biotechnol. 2003 October; 21(10):1179-83; Quake S R, Scherer A, Science. 2000 Nov. 24; 290(5496):1536-40).

In the second use, the device of the present invention is used to diagnose proliferative disease, in particular cancer or tumor, in a subject. Indeed, the device of the present invention allows the determination of the properties of the ring (e.g., morphology, etc. . . . ) as well as the number and the velocity of the cell division.

Accordingly, the present invention concerns a method for diagnosing a proliferative disease in a subject or a method for obtaining information useful for diagnosing a proliferative disease in a subject, comprising:

providing a device according to the present invention bearing cells from a subject sample;
assessing the closure of the ring of the cells; and,
comparing the closure of the ring of the cells to the closure of the ring of reference cells.

In particular, the step a) comprises providing cells from the subject sample to be tested; selecting a device according to the present invention adapted for the provided cells and placing the cells on the device.

In a first embodiment, the reference cells are healthy cells (i.e., cells not suffering of proliferative disorder). Accordingly, a significant difference of the ring closure may be indicative of a proliferative disorder or disease. In a second embodiment, the reference cells are cells affected by a proliferative disorder and the absence of a significant difference of the ring closure may be indicative of a proliferative disorder or disease.

In a first embodiment, the step of assessing the closure of the ring comprises the measure of the number of cells having an open ring and of the cells having a closed ring. In this embodiment, the closure is significantly different in presence and in absence of the test molecule when the number of opened and closed ring is significantly different from the reference. In a second embodiment, the step of assessing the closure of the ring comprises the measure of the velocity of the ring closure. In this embodiment, the closure is significantly different from the reference when the velocity is significantly different from the reference. In a third embodiment, the step of assessing the closure of the ring comprises both the measure of the number of cells having an opened ring and of the cells having a closed ring and the measure of the velocity of the ring closure. In a fourth embodiment, the step of assessing the closure of the ring comprises registering the cytokinetic ring for several cells and determining the form of the superposition of the rings.

In another embodiment and in the context of cells with a cell wall and having an oval or rod shape, the devices according to the invention are also useful to observe any plane perpendicular to the long axis of the cells. Preferably, the cells are yeast. The tip growth of yeast is an interesting phenomenon for the scientific community but it cannot be easily observed with the available devices. Therefore, the device of the invention provides the means to conveniently observe the tip, and then the tip growth.

Therefore, the present invention also concerns a method for observing a plane perpendicular to a long axis of cells with cell wall and having an oval or rod shape, comprising a) providing a device according to the present invention bearing the cells; and b) observing the plane parallel to the observation plane.

The present invention further concerns the use of a device according to the present invention for observing a plane perpendicular to a long axis of cells with cell wall and having an oval or rod shape with a parallel arrangement to the observation plane. In a preferred embodiment, the observed perpendicular plane is the tip of the cells.

In addition, the present invention concerns the use of a device according to the present invention for screening or identifying a test molecule able to modulate the tip growth of cells with cell wall and having an oval or rod shape. More specifically, it concerns a method for screening or identifying a test molecule able to modulate the tip growth of cells with cell wall and having an oval or rod shape comprising:

providing a device according to the present invention bearing cells which have been contacted with a test molecule;
observing the tip growth of the cells;
comparing the tip growth of the cells in presence and in absence of the test molecule; and,
selecting the test molecule for which the tip growth is significantly different in presence and in absence of the test molecule, thereby identifying a test molecule able to modulate the tip growth.

The molecules able to modulate the tip growth, in particular inhibit the growth, present an interest for preventing the microorganism growth. Then, they can be used as anti-bacterial or anti-fungal drugs.

Further aspects and advantages of the present invention will be disclosed in the following experimental section, which should be regarded as illustrative and not limiting the scope of the present application.

EXAMPLES

Cell Division is Unaltered in the Microfabricated Substrates.

The inventors controlled that their method did not affect normal cell growth. The cells had the same treatment (nitrogen starvation, centrifugation, temperature, see Methods), and were subsequently allowed to grow either vertically in wells, here named egg-cups, according to the invention or horizontally on lectin coated substrates (see FIG. 2). The same velocities for growth and division were obtained in both conditions. In addition, the inventors checked that the velocity for ring closure was similar to normal exponential growth conditions with no prior treatment (starvation, centrifugation). Altogether these experiments show that the protocol of the invention does not perturb cell growth.

Cytokinetic Ring Closure can be Visualized in a Single Plane of Focus

Figure 4A:
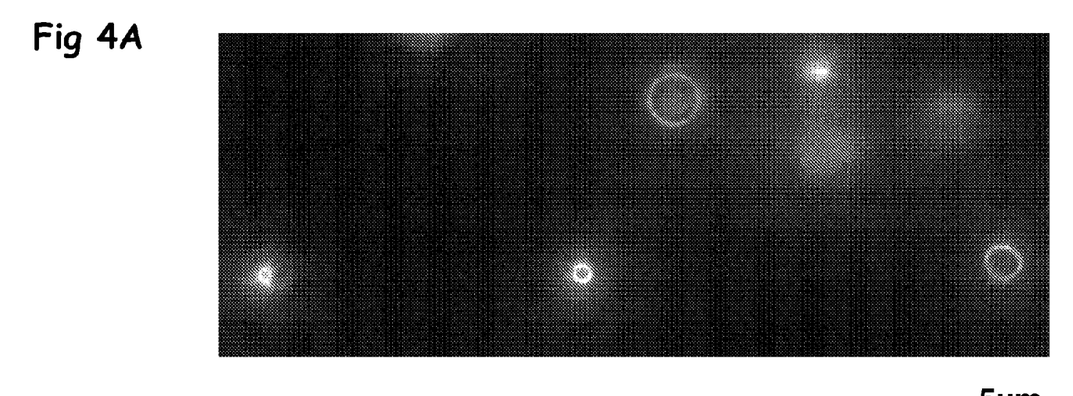
FIG. 4A/Statics: multiple rings are visualised on the same frame.
Figure 4B:
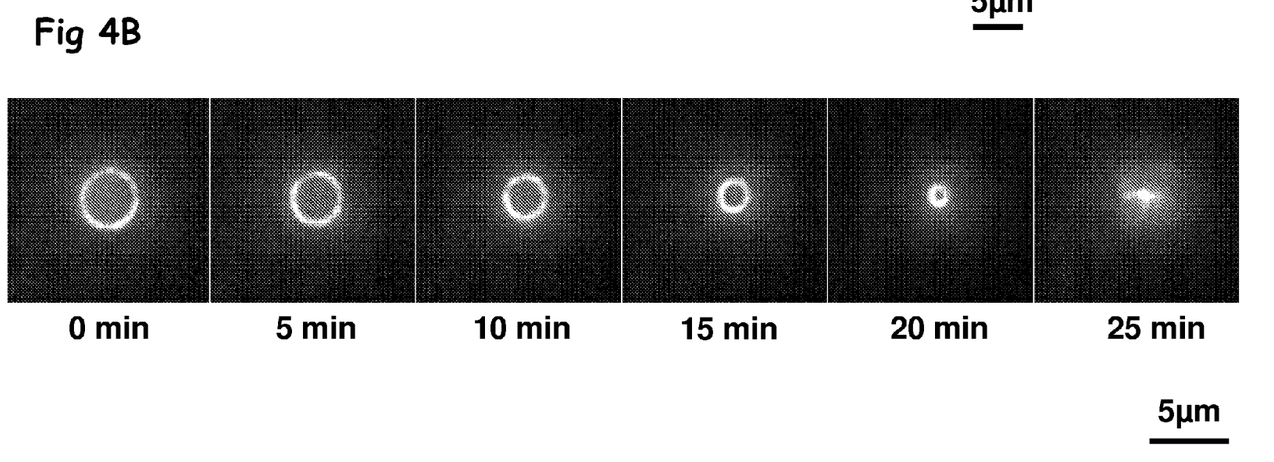
FIG. 4B/Dynamics: successive frames of a single closing ring (T=27° C.)

The inventors successfully used a variety of ring fluorescent markers (see Methods). Here, they illustrate results with the myosin light chain encoded by rlc1 gene fused to mCherry. FIG. 4 shows a typical sequence of the ring closure.

The following features should be pointed out: (i) the ring remains circular, which proves the proper fixed orientation of cells; (ii) exposure time with our set-up for one image is low, typically 0.3 s, which permits to have an excellent temporal resolution; (iii) the ring keeps a constant width, which is consistent with electron microscopy images of the same structure (Kamasaki et al., 2007); this observation further validates the present method; (iv) the ring remains on the same focal plane with no need for manual or automatic refocusing; since the acquisition is automated, all rings of the same sample can be captured in focus, yielding potentially in one hour $10^5$ to $10^6$ rings with cell synchronisation with this experimental set-up. The present method therefore offers rapid, reliable, and statistically significant shapes for cytokinetic rings.

Known Drugs Altering the Closure

Figure 5A:
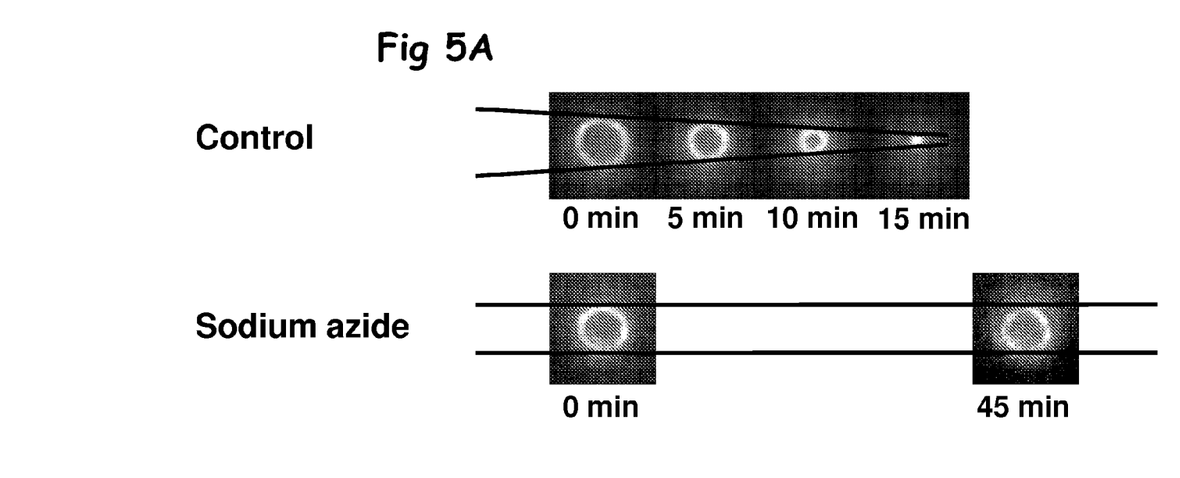
(FIG. 5A) The energy source depletor sodium azide stop the ring closure; note the parallel lines in the presence of the drugs in contrast to the control (T=27° C.).
Figure 5B:
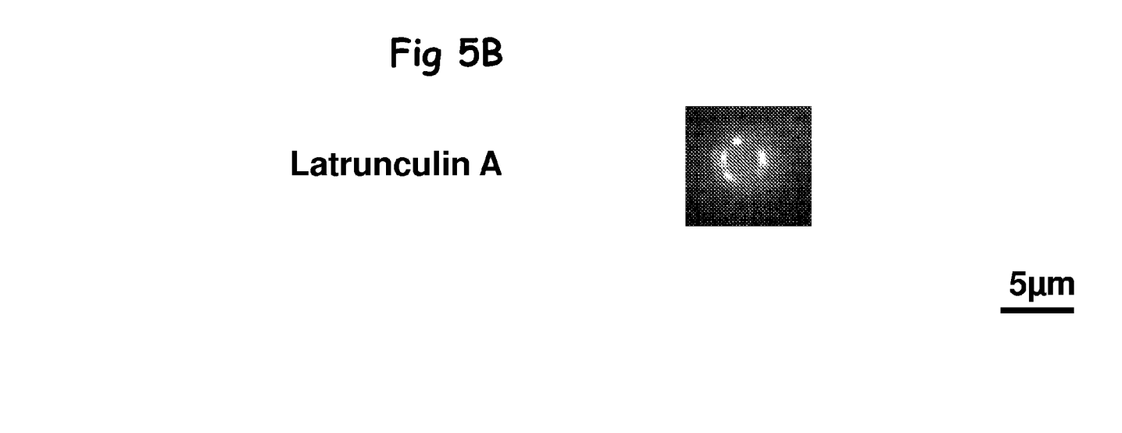
(FIG. 5B) The actin polymerisation inhibitor latrunculin A disrupts the ring.

Myosin activity (Kamasaki et al., 2007) and actin polymerisation (Pelham and Chang, 2002) have been shown to be involved in the closure of the cytokinetic ring. The inventors incubated the cells with latrunculin A (2 μM), a drug known to bind monomeric actin and therefore preventing its polymerisation (Ayscough, 1998). As shown on FIG. 5B, the closure was stopped: the ring disassembled, and this led to the clustering of myosin into discrete patches. The inventors also incubated cells with the metabolic inhibitor sodium azide (Doyle and Botstein, 1996) (20 mM): the closure was stopped as well (see FIG. 5A). Both results where specific inhibitors stop the contraction further demonstrate the reliability of the present approach.

Closure Velocity Depends on the Temperature

Figure 6:
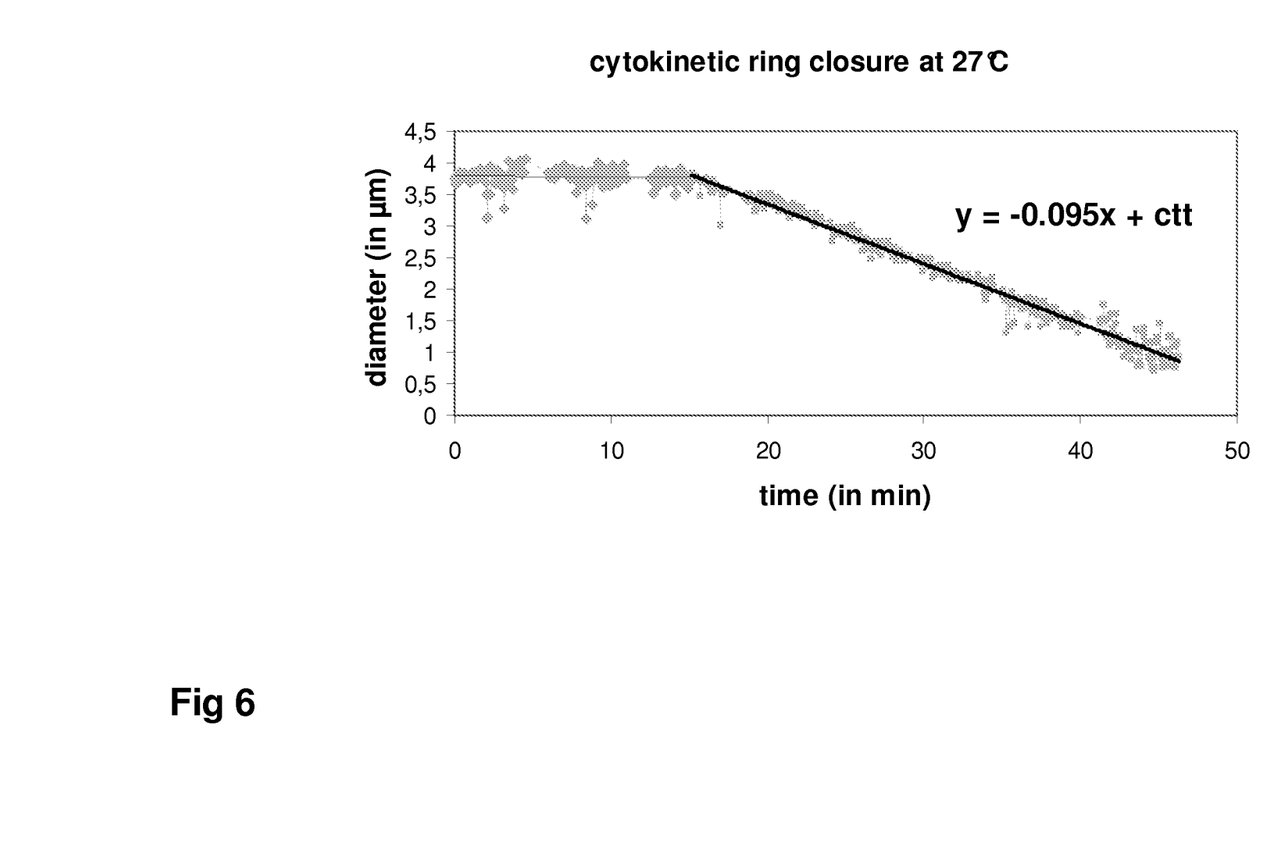

It was shown that the decrease in diameter is linear with time (Pelham and Chang, 2002): the inventors checked that this relation was also linear in this experimental set-up (see FIG. 6). In addition, closure velocity was shown to be strongly dependent on temperature (Wu et al., 2003); this was also observed in this set-up, the velocity was increasing with temperature: 15 nm/min at 18° C., 95 nm/min at 27° C., and 130 nm/min at 36° C.

Finally, velocities at given temperatures were similar to velocities already reported in the literature (Pelham and Chang, 2002; Wu et al., 2003). This further proves that cytokinetic rings are exhibiting normal dynamics with the present method.

Materials And Methods

Microfabrication

The procedure is described here for one filter (see FIG. 3). However it is easily performed with ten filters simultaneously. The polydimethylsiloxane (PDMS) was thoroughly mixed with its curing agent (Sylgard 184, Dow Corning) in a 10:1 ratio. The solution was allowed for degassing for 30 minutes. A porous membrane filter (pore diameter 5.0 μm, shiny face up, Millipore Isopore, TMTP01300) was placed at the bottom of a Petri dish. The gluing side of a simple face tape was applied on top of the filter. The tape with the filter was removed and glued onto a double sided tape attached to a Petri dish with the filter side exposed to the air. The PDMS was poured onto the filters (non shiny face up) and the mixture was allowed to cure overnight; this step was followed by a four hours final curing at 65° C. The stamp was then carefully peeled off. It was exposed to a plasma cleaning for 1 minute (Harrick Plasma, PDC-32G, high setting power), followed by a 10 minutes exposure to Chlorotrimethylsilane 97% (Sigma-Aldrich, C72854, TMCS) vapour.

The liquid degassed PDMS mixture was spread on a glass coverslip #0 (25 mm in diameter, Fisherbrand) with a Pasteur pipette (Balaban et al., 2001), after its cleaning with a 1 minute exposure in the plasma cleaner. The silanised stamp was then placed onto the PDMS coated coverslip, and allowed to cure at room temperature overnight. This was followed by a four hours final curing at 65° C. The stamp was carefully separated from the coverslips, generating the egg cups pattern on the upper layer of the 30 μm thick elastomer. The coverslip was used as the sealed bottom of the chamber; the overall thickness of the sample allowed to use objectives with small working distances and high numerical apertures. For separate experiments where cells were observed in regular horizontal conditions, lectin (25 μl at 100 μg/ml, Sigma, L2380) was dried on the coverslips in order to promote cell adhesion.

Note that larger surfaces can be prepared by using larger filters (up to 14 cm in diameter) with the same method. Any hole sizes can be selected, depending on the cell type; here the inventors matched the 5 μm pore size to the diameter of yeast, but these commercially available membrane filters will be used for preparing egg cups with pore sizes ranging from 500 nm for bacteria to 12-20 μm for mammalian cells (Millipore Isopore, and GE Osmonics Labstore Poretics). In addition, regular arrays of egg cups surfaces can be prepared using standard lithographic methods.

Strains, Medium and Reagents

Standard methods were used for cell growth (Moreno et al., 1991). Briefly, cells were growing exponentially in EMM4S (Moreno et al., 1991), and experiments were conducted using the same medium in the chamber.

*S. pombe* strains successfully used in this study were the following:

JM 207 h+ rlc1 mcherry::natR ura- leu- ade-, J. Moseley
JW 1110 h+ kanMX6-Pmyo2-mYFP-myo2 ade6-M210 leu1-32 ura4-D18, J.-Q. Wu (Wu and Pollard, 2005)
PPG 5054, h+ leu1-32 ura4-D18 pax::KanMX6 leu1+:: GFPpax+, Pilar Perez Lab (Pinar et al., 2008).
JW 977 h+ cdc15-mYFP-kanMX6 ade6-M210 leu1-32 ura4-D18, J.-Q. Wu (Wu and Pollard, 2005)
519 h− bgs1Δ::ura4+ $P_{bgs}1^+$::GFP-bgs1+:leu1+ leu1-32 ura4-Δ18 his3-Δ1, Pilar Perez (Cortes et al., 2002)

These strains respectively contained the following ring markers:

-rlc1-mCherry myosin II regulatory light chain
myo2-YFP myosin II heavy chain
pxl1-GFP paxillin-like protein Pxl1
cdc15-YFP membrane-cytoskeletal interactions, F-BAR domains
bgs1-GFP 1,3-beta-glucan synthase catalytic subunit Bgs1

Finally, the inventors used latrunculin A (Sigma, L5163) at 2 μM, and sodium azide (Sigma, S2002) at 20 mM.

The same experimental method could be efficient on fixed cells. Cytokinetic rings of any cell types would be captured by immunofluorescence with cytoskeleton labelling (myosin II antibody (Straight et al., 2003), or fluorescently labelled phalloidin for example). Finally, rings of cells in the entire samples would be scanned by the automated acquisition set-up.

Experimental Chamber Preparation

Cells were grown in exponential phase at 32° C. At about 0.5 optical density, the EMM4S medium was removed twice by centrifugation at 1000 g for 2 min followed by cells resuspension in a EMM-N medium (Moreno et al., 1991): cells were nitrogen starved at 32° C. for 5 hours. Cells were then pelleted with a 2 min centrifugation at 1000 g and they were resuspended in EMM4S. The egg cup surface (face up) was carefully placed on the top of a home-made plastic holder deposited in a 50 ml tube (adapted from the set-up used by (Allen et al., 2007)); 13 ml of EMM4S was poured in the tube. Cells were exposed to sonication 30 s (Branson 200, Ultrasonic Cleaner) to separate aggregated cells, and 1 ml of cell suspension was added to the 50 ml tube. Cells were then centrifuged at 500 g for 2 mn on the egg-cup surface resting on the special plastic holder. The egg cup surface was carefully removed from the holder and it was inserted in a homemade chamber (see FIG. 2D). The sample preparation was achieved by screwing a top metal piece onto the surface holder. Fresh medium (EMM4S, 3 ml) was immediately added to the formed chamber.

Eight additional washes with fresh EMM4S were then performed by pipetting up and down the medium in the chamber, in order to remove cells not embedded in wells. Efficient removal of cells was checked during washes and was further confirmed under the microscope. A top cover was added to the sample to prevent evaporation, and the sample was placed in the incubator of the target temperature. For 25° C. observations, after 10 hours, ring closures were observed.

Microscopy

Cells were observed with two different setups: the Deltavision acquisition system (Applied Precision), and an Olympus CKX41 inverted microscope (Olympus) equipped with the Wasabi acquisition system (Hamamatsu) and a cooled couple-charged device camera (C4742-96-12G04 Hamamatsu) and a shutter (Uniblitz, Vincent Associates). The following objectives were used: 100× UPlanF1 objective (Ph3, 1.3 NA, Olympus), 100× UPlanSApo objective (1.40 NA, Olympus), and a 60× PlanApo objective (1.45 NA, Olympus). Experiments were performed with a temperature control unit (WeatherStation for Deltavision, or a temperature control via the oil immersion objective (Riveline et al., 1998)). Images were processed with Wasabi software (Hamamatsu) or ImageJ.

REFERENCE

Allen, T.D., S.A. Rutherford, S. Murray, H.S. Sanderson, F. Gardiner, E. Kiseleva, M.W. Goldberg, and S.P. Drummond. 2007. Generation of cell-free extracts of Xenopus eggs and demembranated sperm chromatin for the assembly and isolation of in vitro-formed nuclei for Western blotting and scanning electron microscopy (SEM). *Nat Protoc* 2(5): 1173-1179.

Ayscough, K. 1998. Use of latrunculin-A, an actin monomer-binding drug. *Methods Enzymol* 298:18-25.

Balaban, N.Q., U.S. Schwarz, D. Riveline, P. Goichberg, G. Tzur, 1. Sabanay, D. Mahalu, S. Safran, A. Bershadsky, L. Addadi, and B. Geiger. 2001. Force and focal adhesion assembly: a close relationship studied using elastic micropatterned substrates. *Nat Cell Biol* 3(5):466-472.

Collado, M., J. Gil, A. Efeyan, C. Guerra, A.J. Schuhmacher, M. Barradas, A. Benguria, A. Zaballos, J.M. Flores, M. Barbacid, D. Beach, and M. Serrano. 2005. Tumour biology: senescence in premalignant tumours. *Nature* 436(7050):642.

Cortes, J.C., J. Ishiguro, A. Duran, and J.C. Ribas. 2002. Localization of the (1,3)beta-D-glucan synthase catalytic subunit homologue Bgs1p/Cps1p from fission yeast suggests that it is involved in septation, polarized growth, mating, spore wall formation and spore germination. *J Cell Sci* 115(Pt 21):4081-4096.

Doyle, T., and D. Botstein. 1996. Movement of yeast cortical actin cytoskeleton visualized in vivo. *Proc Natl Acad Sci USA* 93(9):3886-3891.

Jackson, J.R., D.R. Patrick, M.M. Dar, and P.S. Huang. 2007. Targeted anti-mitotic therapies: can we improve on tubulin agents? *Nat Rev Cancer* 7(2):107-117.

Kamasaki, T., M. Osumi, and I. Mabuchi. 2007. Three-dimensional arrangement of F-actin in the contractile ring of fission yeast. *J Cell Biol* 178(5):765-771.

Lang, P., K. Yeow, A. Nichols, and A. Scheer. 2006. Cellular imaging in drug discovery. *Nat Rev Drug Discov* 5(4): 343-356.

Liu, J., H. Wang, D. McCollum, and M. K. Balasubramanian. 1999. Drc1p/Cps1p, a 1,3-beta-glucan synthase subunit, is essential for division septum assembly in Schizosaccharomyces pombe. *Genetics* 153(3):1193-1203.

Mathon, N.F., and A.C. Lloyd. 2001. Cell senescence and cancer. *Nat Rev Cancer* 1(3):203-213.

Moreno, S., A. Klar, and P. Nurse. 1991. Molecular genetic analysis of fission yeast Schizosaecharomyces pombe. *Methods Enzymol* 194:795-823.

Pelham, R.J., and F. Chang. 2002. Actin dynamics in the contractile ring during cytokinesis in fission yeast. *Nature* 419(6902):82-86.

Pinar, M., P.M. Coll, S.A. Rincon, and P. Perez. 2008. Schizosaccharomyces pombe Px11 is a paxillin homologue that modulates Rho1 activity and participates in cytokinesis. *Mol Biol Cell* 19(4):1727-1738.

Riveline, D., A. Ott, F. Julicher, D.A. Winkelmann, 0. Cardoso, J.J. Lacapere, S. Magnusdottir, J.L. Viovy, L. Gorre-Talini, and J. Prost. 1998. Acting on actin: the electric motility assay. *Eur Biophys J* 27(4):403-408.

Straight, A.F., A. Cheung, J. Limouze, I. Chen, N.J. Westwood, J.R. Sellers, and T. J. Mitchison. 2003. Dissecting temporal and spatial control of cytokinesis with a myosin II Inhibitor. *Science* 299(5613): 1743-1747.

Sun, Q., and W. Margolin. 1998. FtsZ dynamics during the division cycle of live Escherichia coli cells. *J Bacteriol* 180 (8):2050-2056.

Weibel, D.B., W.R. Diluzio, and G.M. Whitesides. 2007. Microfabrication meets microbiology. *Nat Rev Microbiol* 5(3):209-218.

Wu, J.Q., J.R. Kuhn, D.R. Kovar, and T.D. Pollard. 2003. Spatial and temporal pathway for assembly and constriction of the contractile ring in fission yeast cytokinesis. *Dev Cell* 5(5):723-734.

Wu, J.Q., and T.D. Pollard. 2005. Counting cytokinesis proteins globally and locally in fission yeast. *Science* 310 (5746):310-314.

The invention claimed is:

1. A device for observing the cytokinetic ring of cells comprising a support and a microfabricated substrate bearing a plurality of wells, wherein one or more of the plurality of wells contain a single cell and orient the closure plane of the cytokinetic ring of said cell parallel to the observation plane to provide for the observation or imaging of the entire cytokinetic ring at a single time point, and wherein the width of the individual wells is less than the depth of wells and the width of the individual wells is about the diameter of a round cell or the width of the individual wells is about the diameter of the short axis of the cell having oval or rod form.

2. The device according to claim 1, wherein the width of the individual wells is about the diameter of round cells.

3. The device according to claim 1, wherein the width of the individual wells is about the diameter of the short axis of the cell for cells which have oval or rod form.

4. The device according to claim 1, wherein the cells have a cell wall and the depth of wells is at least or about ½ of the cell long axis.

5. The device according to claim 1, wherein the cells are yeast, the well width is between 1 to 6 μm or between 3 to 5 μm, and the well depth is between 4 to 10 μm or between 6 to 8 μm.

6. The device according to claim 1, wherein the cells are bacteria and the well width is between 500 nm and 3 µm.

7. The device according to claim 1, wherein the cells are devoid of cell wall and the device further comprises a top covering the wells, the well depths being about a cell diameter in depth, and the bottom of the wells and the top being coated by molecules that promote cell attachment and the top covering being configured to contact a cell placed in a well of the device.

8. The device according to claim 7, wherein the molecules that promote cell attachment are fibronectin.

9. The device according to claim 7, wherein the well depths and width are about 10-50 µm or about 12-20 µm.

10. The device according to claim 1, wherein the thickness of the support and the microfabricated substrate is less than 200 µm or less than 150 µm or between 100 and 150 µm.

11. The device according to claim 10, wherein the support is a plate of glass.

12. The device according to claim 10, wherein the microfabricated substrate is made of poly(dimethylsiloxane) (PDMS).

13. The device according to claim 1, wherein the device further comprises physical barriers separating several groups of wells from each other on the device.

14. The device according to claim 13, wherein the device further comprises microfluidic system in order to address samples to the groups of wells on the device.

15. A method for observing the cytokinetic ring of cells comprising a) providing a device according to claim 1 bearing at least one cell; and b) observing or imaging the entire cytokinetic ring with the closure plane of the cytokinetic ring parallel to the observation plane at a single time point.

16. A method for screening or identifying a test molecule able to modulate the cell division comprising:
providing a device according to claim 1 bearing at least one cell which has been contacted with a test molecule;
assessing or imaging the closure of the entire cytokinetic ring with the closure plane of the cytokinetic ring parallel to the observation plane at a single time point;
comparing the closure of the cytokinetic ring of the cells in presence and in absence of the test molecule; and
selecting the test molecule for which the closure is significantly different in presence and division.

17. A method for in vitro diagnosis of a proliferative disorder in a subject comprising:
providing a device according to claim 1 bearing a plurality of cells of a sample from the subject;
assessing or imaging the closure of the entire cytokinetic ring with the closure plane of the cytokinetic ring parallel to the observation plane at a single time point; and
comparing the closure of the ring of the cells to the closure of the ring of reference cells.

18. A method for preparing a device according to claim 1 comprising:
providing a filter having a suitable pore diameter and thickness;
putting the filter on a first support such that the bottom side of the pores is closed;
pouring a liquid polymer that might be hardened and after hardening;
peeling off the obtained replica from the filter, thereby providing a template;
optionally, carrying out an anti-adhesive treatment on the template to facilitate the demolding;
spreading another liquid polymer that might be hardened onto a second support;
gently pressing or placing the template against the second support coated with the polymer and, after polymer hardening;
removing the template from the obtained microfabricated substrate, thereby obtaining the device.

19. The method according to claim 18 wherein the filter is a filter with a pore size of between 0.08 and 50 µm and a thickness of between 5 and 25 µm.

20. The device according to claim 5, wherein the well depth is between 6 to 8 µm.

21. The device according to claim 5, wherein the cells are yeast, the well width is between 3 to 5 µm and the well depth is between 6 to 8 µm.

* * * * *